(12) United States Patent
Rapparport et al.

(10) Patent No.: US 10,037,710 B2
(45) Date of Patent: Jul. 31, 2018

(54) PREVENTION AND INTERVENTION ASSISTANCE SYSTEM

(71) Applicant: ePreventions, LLC, Newport Beach, CA (US)

(72) Inventors: Mark Neil Rapparport, Newport Coast, CA (US); Rial Allen Barnett, Irvine, CA (US); Behnmam Shah-Hosseini, Irvine, CA (US); Daniel Albert Cossack, Irvine, CA (US)

(73) Assignee: ePreventions, LLC, Newport Beach, CA (US)

( * ) Notice: Subject to any disclaimer, the term of this patent is extended or adjusted under 35 U.S.C. 154(b) by 692 days.

(21) Appl. No.: 14/569,355

(22) Filed: Dec. 12, 2014

(65) Prior Publication Data

US 2015/0099250 A1    Apr. 9, 2015

Related U.S. Application Data

(63) Continuation of application No. 13/934,181, filed on Jul. 2, 2013.
(Continued)

(51) Int. Cl.
G09B 19/00 (2006.01)
G09B 7/02 (2006.01)
(Continued)

(52) U.S. Cl.
CPC ............... *G09B 19/00* (2013.01); *G09B 5/00* (2013.01); *G09B 7/02* (2013.01); *G16H 10/20* (2018.01)

(58) Field of Classification Search
CPC . G09B 19/00; G09B 7/02; G09B 5/00; G16H 10/20
See application file for complete search history.

(56) References Cited

U.S. PATENT DOCUMENTS

2001/0001852 A1    5/2001   Rovinelli et al.
2001/0013006 A1    8/2001   Brown
(Continued)

OTHER PUBLICATIONS

Monaghan et al., Internet-based Interventions for the Treatment of Problem Gambling, A report prepared for the Centre for Addiction and Mental Health (CAMH); pp. 1-108.
(Continued)

*Primary Examiner* — Nathan Hillery
(74) *Attorney, Agent, or Firm* — Knobbe, Martens, Olson & Bear, LLP

(57) ABSTRACT

Systems and methods for online assisted pre-intervention or "prevention" are described. A prevention system may provide the ability to initiate a prevention campaign in order to create a customized support forum for persons who may be afflicted by a harmful addiction. The prevention system can receive a request to initiate a campaign for a recipient from a host and facilitate the invitation of other participants to the campaign. Knowledge-based questionnaires may be dynamically generated for the host and participants, and a profile built for the recipient based on received responses. Customized messages may be generated by the prevention system using expert knowledge-based rules, and delivered to the recipient. The messages may be unique to the recipient based on the recipient's circumstances and relationship to the host and participants. Support services provided by the prevention system encourage the recipient to agree to accept help and provide action plan recommendations.

5 Claims, 7 Drawing Sheets

Related U.S. Application Data

(60) Provisional application No. 61/667,878, filed on Jul. 3, 2012.

(51) Int. Cl.
  *G09B 5/00* (2006.01)
  *G16H 10/20* (2018.01)

(56) References Cited

U.S. PATENT DOCUMENTS

| | | |
|---|---|---|
| 2001/0041329 A1 | 11/2001 | Legarda |
| 2002/0032581 A1 | 3/2002 | Reitberg |
| 2005/0246185 A1* | 11/2005 | Brown .................. G06Q 50/22 705/2 |
| 2006/0229914 A1 | 10/2006 | Armstrong |
| 2007/0038471 A1* | 2/2007 | Meisel .................. G06Q 50/22 705/2 |
| 2007/0061166 A1 | 3/2007 | Ramasubramanian et al. |
| 2007/0106127 A1 | 5/2007 | Alman |
| 2007/0168501 A1 | 7/2007 | Cobb et al. |
| 2007/0213998 A1 | 9/2007 | Butler et al. |
| 2008/0086325 A1 | 4/2008 | James |
| 2008/0109251 A1 | 5/2008 | Schmitt |
| 2008/0109257 A1 | 5/2008 | Albrecht |
| 2008/0177567 A1 | 7/2008 | Friedlander et al. |
| 2008/0177836 A1 | 7/2008 | Bennett |
| 2008/0201174 A1 | 8/2008 | Ramasubramanian et al. |
| 2009/0132284 A1* | 5/2009 | Fey ....................... G06F 19/322 705/3 |
| 2009/0164917 A1 | 6/2009 | Kelly |
| 2011/0046978 A1 | 2/2011 | Gordon et al. |
| 2011/0047508 A1* | 2/2011 | Metzler ................. G06F 19/322 715/810 |
| 2011/0053128 A1 | 3/2011 | Alman |
| 2011/0172497 A1 | 7/2011 | Ruby et al. |
| 2011/0250576 A1 | 10/2011 | Hester |
| 2012/0046964 A1 | 2/2012 | Papa |

OTHER PUBLICATIONS

Vandemark et al., An explanatory study of engagement in a technology-supported substance abuse intervention, Substance Abuse Treatment Prevention and Policy; http://www.substanceabusepolicy.com/content/5/1/10; pp. 1-14.

* cited by examiner

PREVENTION AND INTERVENTION ASSISTANCE SYSTEM

CROSS-REFERENCE TO RELATED APPLICATIONS

This application is a continuation of and claims priority from U.S. application Ser. No. 13/934,181, filed Jul. 2, 2013, which claims priority from provisional U.S. Pat. App. No. 61/667,878, filed on Jul. 3, 2012, the disclosures of which are each hereby incorporated by reference in their entireties.

BACKGROUND

Addiction can have a crippling and harmful effect not only to an individual suffering from the addiction, but also to loved ones such as family, friends, and co-workers who care for the afflicted individual. Addiction can take on many forms ranging from physical addiction (e.g., substance abuse, alcoholism, etc.) to behavioral or psychological addiction (e.g., compulsive behavior, gambling, etc.). Confronting and dealing with addiction-related problems is often a significant undertaking which may require the guidance or counseling of a trained professional. Concerned loved ones may decide to take action by conducting an intervention, which can be stressful for those involved as well as costly when a trained interventionist is used. In some cases by the time an intervention is conducted, the afflicted individual is so consumed by the addiction that recovery may be prolonged, difficult, and costly.

SUMMARY

This disclosure describes a customized prevention system and methods for intervention assistance to enable family, friends, and/or loved ones of an afflicted individual suffering from, or at risk of an addiction or related disorder (e.g., alcoholism, drug abuse, gambling, or other harmful addictions), to create a personal, customized support forum and messaging system for the individual in order to motivate the individual to take the first step towards recovery. The design of this forum is to encourage, motivate, or otherwise cause the individual (e.g., "a recipient") to recognize that there is a problem and gain the courage to take the first step towards recovery. This may ultimately be in the form of entering a rehabilitation facility or program, or recognizing the problem and how it is affecting those around them and recommending an action plan to take steps towards recovery. This forum empowers the loved ones of the suffering individual to take action in showing their love and support, and enables them to feel like they are doing their part in assisting the at-risk individual towards eventual recovery. To enable a person that has a friend or loved one who is suffering from a curable disease to break the cycle of the disease and to get help. The goal of the system described in the present disclosure is to help persons create an effective customized digital message of love and care to plant a seed of healing and initiate the process of recovery in the life of someone afflicted with an addictive disorder, helping to lead the message recipient into treatment.

The prevention system and methods described herein generally involve an individualized and customized web-based prevention or "pre-intervention" system that enables the relatives, friends, and/or loved ones of an afflicted individual to help motivate the individual to take the first step towards recovery (e.g., entering a recovery program and/or entering a rehabilitation facility, such as before a full-scale intervention becomes necessary, or when financial constraints don't make an intervention feasible). The prevention system facilitates the creation and delivery of pre-configured and approved messages sent on behalf of the concerned individuals to the afflicted individual. The prevention system also enables the creation and delivery of customized written, audio, and/or video messages that have obtained the input and support of a trained professional (e.g., a "preventionist"). A "host" (e.g., a loved one seeking to help an at-risk individual) may begin the prevention process, and invite other guests (e.g., family/relatives, friends, and co-workers) to participate in the prevention.

The host first creates an account with the prevention system and, in some embodiments, pays for the "prevention." The Host then goes through the process of answering a series of questions that are provided to the prevention system and entered into an expert rules engine. The expert rules engine may include or have access to, for example, a rules based knowledge database that is configured to gain intelligence as it receives input from the host and participants. As they describe the circumstances necessitating the prevention, providing further details about the intended recipient's specific situation, sharing their personal thoughts and feelings about the circumstances and the recipient, the prevention system generates a motivational message based on the various input criteria. Through the prevention system, a customized and personal message is generated for delivery to the recipient via a variety of means including for example delivery and/or presentation via email, text message/SMS, mobile application (e.g., for iOS, Android, Windows Mobile, and other mobile operating systems), as well as via desktop and laptop computers. In some embodiments, the host may recruit additional co-hosts to create their own support messages and/or make donations for the recipient to attend a treatment program which may be accessed, for example, via a website or service provided by the prevention system. Each co-host may follow a similar procedure to create written, audio, or video message. In some embodiments involving added personal content, the host and a trained professional counselor (e.g., a "preventionist") may review all customized messages before the final message and/or invitation to join the prevention is delivered to the recipient. The message and/or invitation may then be sent to the recipient.

The message may be generated and provided in a variety of different formats and contain a variety of different levels of content. The message can range from a simple wall of pre-configured and semi-customized letters/cards to an entire customized room where the person can listen to and watch the personalized audio and video messages from his loved ones. The prevention computing system may deliver the invitation to the person via email, text, and/or voicemail. When the recipient receives the message and accepts the notice to join the prevention he/she may be greeted by the host, who will be the first point of contact. In some embodiments, the host's customized message may be delivered first, and the recipient may be presented an opportunity to read, watch, and listen to the other personalized messages of love, support, and concern. The message recipient will then have the opportunity to say "Yes" to accept help and begin the recovery process.

As described herein, a prevention (sometimes referred to as a "prevention campaign) may be generally thought of as a "pre-intervention". One purpose of the prevention is to reach out to a loved one to express concern over his/her addiction (e.g., drug and/or alcohol use). The prevention computing system enables users to reach out before it becomes time for a full intervention, and to plant the seed of healing when for whatever reason an intervention may not be feasible. The purpose is to support a loved one getting the necessary help to start recovery from the disease of substance abuse. The prevention system allows users to notify the recipient in a warm, non-threatening, caring way with messages created and sent from friends and loved ones who have taken the time because they care. Friends and loved ones are hopeful that the recipient will acknowledge that the problem will only get worse and to accept help before that happens. The emphasis is on planting a seed, dispelling denial, and inspiring the recipient to take the first step to accept help. A prevention may be initiated via the prevention system when it is evident that a person needs help (e.g., participation in some form of in-patient treatment, sober living, or meetings) but has not taken the action on his/her own. In some cases an actual professional intervention may be more appropriate, and the preventions system may provide such a recommendation after an initial qualifying questionnaire is responded to by a user who wishes to initiate a prevention. In some instances, the prevention system may offer an upgraded version that utilizes the support and advisory services of a trained professional with the equivalent training and expertise of an Interventionist.

One benefit of the prevention system is that it differs from a traditional intervention. The prevention system utilizes an expert system to advise the participants on how to create an effective message, follow established protocol in dealing with addictive disorders (e.g., via a web site or application) as an effective method of helping their loved one and/or as a helpful preparation for a potentially necessary engagement by a team or professionals in a more traditional treatment setting. The purpose of an Intervention is generally to get the recipient into a treatment program or sober living environment-as either a first step towards a full blown intervention, or as a step to reach out to a person again after they may have relapsed. The digital tools offered by the prevention system can enable an interventionist to utilize all of the information gathered during a prevention to save time and increase the efficacy of the intervention, should that step be needed in the eventual treatment of the disease. Generally there are higher costs associated with interventions, which combined with other factors can make them not feasible for certain persons. Thus, a prevention can directly assist in the important fact gathering for an intervention, setting up and preparing for this more involved and time consuming alternative. The prevention is not intended to supplant the intervention. Rather, a prevention can be either a lower cost alternative, a source of re-enforcement, or provide an important bridge to an intervention.

Embodiments of the prevention system as described herein can provide a number of benefits. First, the prevention system leverages the latest technology tools to provide a safe, effective, and customized forum so that afflicted individuals who are or may be suffering from an addictive disorder, such as alcoholism or drug addiction, can begin the process of recovery and gain a sense of control and power over what might otherwise be an out of control situation. For example, video mapping may be used to filter content from input about an individual suffering from an addiction and match it to content in a specific video or video library. Second, the prevention system creates a healthy environment where an afflicted individual (e.g., a recipient) suffering from alcoholism and/or other unhealthy addictions can receive a pre-intervention message (e.g., a "Prevention") and know that he/she is not alone and that there is a support group sending personalized messages of love, support, and concern, from people who are willing to do their part in helping the afflicted individual recognize the problem and help motivate him/her to take the first step toward recovery. The prevention system also enables the afflicted individual to start the process of healing by planting the seed and progressing to taking the all important first step towards recovery. This also enables caring people (e.g., a host and participants) to feel they are doing something positive to help, giving them a sense satisfaction and self-empowerment of knowing they are doing something to help the loved one threatened or consumed by addiction.

In one embodiment, the prevention system may be a web based system that enables a host customer (such as an individual motivated to help a friend or loved one suffering from alcohol, drug abuse or other addiction disorders) to create a message of love and caring to a recipient (such as the friend or loved one suffering from the addiction disorder), and then deliver the message via the internet in a format optimized for a variety of viewing platforms, including but not limited to, for example, cell/smart phone, tablet, portable/mobile computing device, desktop, laptop, or personal computer.

DETAILED DESCRIPTION

Overview

Figure 1:
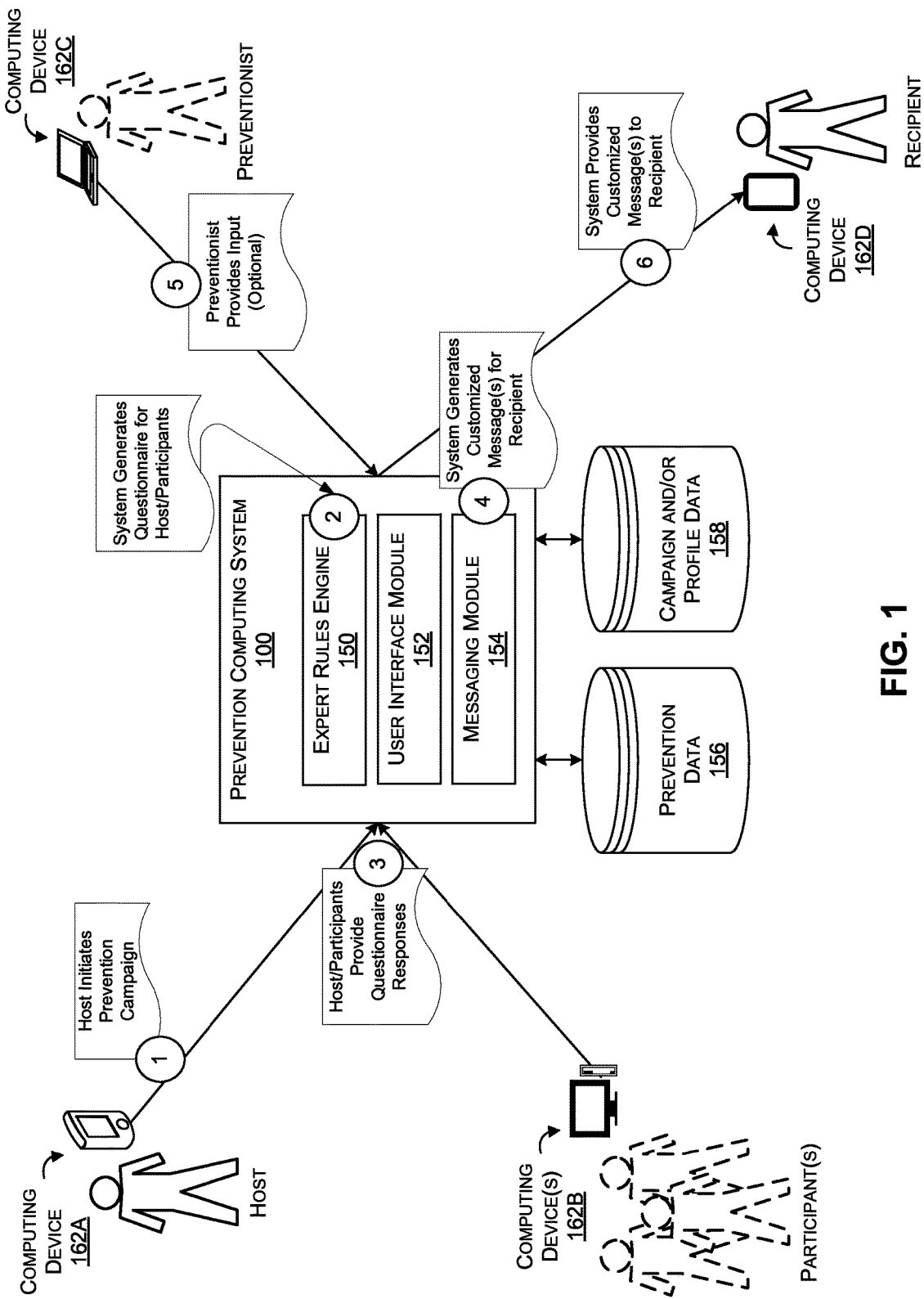
FIG. 1 is a block diagram which illustrates an exemplary data flow between an individual's computing device and a prevention computing system, according to one embodiment.

As described herein, a prevention computing system (or simply "prevention system") enables and facilitates a pre-intervention "prevention" campaign on behalf of one or more individuals who wish to provide help for an afflicted loved one. As used herein, a host is the person/individual who initiates a campaign, identifies a recipient of the message, and invites other participants to join. The host controls the campaign and makes the final approval to deliver the message to the recipient. The recipient is the person to whom the message is intended for, and whom the host has identified as the target of the campaign. A participant is a person invited by the host to join the campaign. The participant can be, for example, a friend, a relative, a co-worker, or other individual concerned for the well-being of the recipient. A preventionist may be, for example, a professional counselor who may get involved in a campaign to assist the host and participants in the creation of the message.

A campaign refers generally to the process of a specific prevention. A campaign starts with the host creating an account with the prevention system and identifying the recipient. A campaign may end with the final delivery of the message to the recipient. The campaign process may involve viewing a video on a subject related to a disorder and/or the intervention and prevention processes, filling out a questionnaire, inviting other participants to the campaign, creating a message for the recipient, and delivering the message to the recipient. A campaign definition may define what is included in a particular campaign for a specific problem (e.g., an illness, addiction/disorder, disease, or similar issue to be addressed in the prevention). The campaign may include a questionnaire comprising one or more question sets, each question set comprising one or more questions that are part of the questionnaire. In some embodiments involving the presentation or display of a user interface to the host and/or participants completing the questionnaire, a page group may be defined as part of the questionnaire, wherein the page group is identified as a group of questions that can be displayed on a single page or user interface screen.

Each campaign may be targeted toward a specific problem. For example, one type of campaign may be designed to address alcoholism, another type of campaign may be designed to address drug addiction (or multiple types of campaigns for each of multiple types of drug addictions), another type of campaign for gambling addiction, and so on. The campaign definition may include a list of items that are needed to fulfill a specific type of campaign. The items listed may include questionnaire sets, videos and other media, action definitions, and other reference material. A campaign container may be created at the start of any new campaign and configured to store the progress and results of the campaign as it progresses. For example, this may include a list of participants, and questions and answers to questions asked of the participants.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

High Level Process and Data Flow

FIG. 1 is a block diagram which illustrates an exemplary process and data flow between a host (e.g., via a computing device 162A), one or more participants (e.g., via one or more computing devices 162B), an optional preventionist (e.g., via a computing device 162C), a recipient (e.g., via a computing device 162D), and a prevention computing system 100, according to one embodiment. The data flow of FIG. 1 illustrates how the host can initiate a prevention campaign, via the prevention computing system 100, to generate and deliver a customized message to the recipient.

Beginning at step (1), the host initiates a prevention campaign with the prevention computing system 100. This process may include creating an account for the host and presenting a short orientation video to the host. The host may invite other participants to the campaign, such as family members, friends, or co-workers. In one embodiment, only the host may invite other participants.

In one embodiment, initiating the prevention campaign may involve, for example, providing responses to a qualifying questionnaire and/or inviting one or more participants to participate in the prevention campaign. The qualifying questionnaire may contain certain key questions which are asked to initialize a campaign and verify an appropriateness of a message to be generated. The qualifying questionnaire may also be used to qualify the worthiness and need for treatment of the message recipient in accordance with applicable Health Insurance Portability and Accountability Act ("HIPAA") laws and regulations and professional industry guidelines and practice for the treatment of persons with particular addiction symptoms.

At step (2), the prevention computing system 100 generates a questionnaire for the host and/or for the participants. As will be further described, in some embodiments the questionnaire may be generated iteratively using a variety of machine-based learning techniques and/or knowledge-based rules, such that responses or answers to a first question (or question set) received from the host and/or the participants may be used to determine the next question (or question set) that may be provided as part of the questionnaire, and so on until the questionnaire has been completed. The questions provided in the questionnaires may be based on data accessed, for example, from a preventions data source 156. The preventions data 156 may store, for example, subject matter data for a variety of disorders, expert or knowledge-based rules related to the subject matter data, and/or pre-defined questions. The prevention computing system 100 may access the prevention data 156 and, via an expert rules engine 150, determine and/or generate questions to be provided as part of the questionnaire based at least in part on the accessed prevention data (e.g., subject matter data for disorders and/or related knowledge-based rules for the subject matter). This process is illustrated and described in more detail with reference to FIG. 4 herein.

At step (3) the questionnaire is provided to the host and/or participants, who then provide responses to the prevention computing system 100. The questionnaire may be provided, for example via a user interface generated by a user interface module 152 of the prevention computing system 100. The user interface may be configured for display on computing devices 162A and 162B. As the prevention computing system 100 receives the questionnaire responses, a profile for the recipient may be created and updated based on the questions and received responses. The profile may be stored for example in a campaign and/or profile data source 158, along with other data related to the campaign, the host, and/or the participants of the campaign.

The process and data flow at steps (2) and (3) may be repeated an indefinite number of times until the questionnaires have been completed by the host and/or participants. The length and type of questionnaire provided may vary depending on a type of disorder, the nature of the recipient's condition as indicated by the received responses, and other factors. In some embodiments, as information about the recipient is received and collected by the prevention computing system 100, the system may use the information to determine and provide relevant questions to the other participants. Thus the prevention computing system 100 may utilize what it has learned through the questionnaire process and express the knowledge it has already gained from the previous questions asked.

At step (4), the prevention computing system 100 utilizes the data collected through the questionnaire/input process to generate a customized message to the recipient. The message may be generated, for example via a messaging module 154, based on a series of pre-established recommendations and/or prompted preloaded information, which may be stored and accessed from the prevention data source 156. In one embodiment, the message may be a basic message which is restricted to content that the prevention system generates because the host and/or participants may not necessarily be qualified to make decisions about important variables and appropriate content. In some embodiments, a unique and personal message may be generated for each of the host and participants, and the host may have access to view each of the messages and decide to use or not use any of the messages for delivery to the recipient. According to one embodiment, the host will make the final decision to begin the delivery process.

In another embodiment, the host may also choose or enroll in an enhanced service to access help from a professional counselor (e.g., a "preventionist"). Thus, at step (5) the preventionist may get involved in the campaign to, for example, assist the host and participants in the creation of the message. The preventionist may provide an assisted delivery option by providing input for the customized message. In some embodiments, when the host has enrolled to access the services of the preventionist, the prevention system may grant the host to with administrative access and/or additional privileges which may allow the host to make changes to be made to the message, including allowing the host and/or participants to add personal letters, photos, videos, and other content. The preventionist may be involved in this process to ensure that any additional, personalized content is still appropriate for the recipient's particular disorder or circumstances.

At step (6), the prevention computing system 100 provides the customized message to the recipient. The customized message may be provided to the recipient in a variety of formats including electronic mail ("email"), text message (Short Message Service ("SMS") or Multimedia Message Service ("MMS")), HTML 5.0 optimized messages for smartphones/tables, and so forth. In some embodiments, the customized message may include an option or invitation for the recipient to view the message on a web page provided by the prevention computing system 100. The customized message may also provide an option for the recipient to agree to accept help, which may prompt the prevention computing system 100 to create an account for the recipient. In some embodiments, the prevention computing system 100 may repeat step (6) an indefinite number of times by periodically sending additional customized messages generated by the prevention computing system 100 and selected by the host.

In FIG. 1, the prevention data source 156 and campaign and/or profile data source 158 are shown as stand-alone data stores accessible by the prevention computing system 100. In some embodiments, such as the embodiment of the prevention computing system 100 shown in FIG. 7, the prevention data source 156 and campaign and/or profile data source 158 may be included as part of the prevention computing system 100.

Examples of Question Generation and Data Gathering Methods Performed by a Prevention Computing System The prevention computing system 100 of FIG. 1 includes an expert rules engine 152 (also referred to as a knowledge based rules engine herein) which gathers information about a person afflicted with an addictive disorder, stores it in a digital format (e.g., in the campaign and/or profile data store 158), and then processes the inputs through a series of detailed questions that become more specific and tailored to the individual as the system accumulates knowledge about the person. The purpose of this questioning is to gather information about a person suffering from an addictive disorder, rendering intelligent advice and then making specific recommendations of actions for treatment based on expert rationale on how and where to get help that is based on established treatment protocols and extensive industry knowledge. It is a type of inference engine that utilizes mixed chaining methodologies to build an output recommendation based on the processing of various input data. The rules engine may implement knowledge engineering techniques which involve learning to ask more specific and appropriate questions as a profile on the person is built and/or updated as information is provided to it, allowing it to further refine the specificity, appropriateness, and accuracy of its output based on the intelligence in the system. The expert rules engine 152 may also be contributed by a "subject matter expert" ("SME") which establishes the extensive rule sets. The expert rules engine 152 may be configured to recognize fact patterns and preferences so that it can match the input criteria with specific output actions including, treatment recommendations, suggested action steps to be taken, as well offer advice and recommendations for the usage of specific experiential content during the message creation process.

The prevention computing system 100 may use "circumstantial questioning" to ask questions in order to identify the degree of disease progression and barriers established by the recipient to deny the existence of the disease. Thus, the prevention computing system 100 learns from the last question as it formulates the next one to ask. This may be thought of as a conversational inference engine which gathers pertinent information necessary to begin processing an output (e.g., a message and/or an action plan for the recipient), using a combination of chaining methods (e.g., mixed chaining, backward chaining, etc.) such that an ultimate determination can be made about the exact condition of the person's disease progression and the best recommendation that can be made to treat it.

In some instances, input process implemented by prevention computing system 100 may involve a standard fault diagnosis method to accumulate information that is later utilized to establish an output. Using an underlying backward chaining technique, simple confirmations may be made. For example, once certain questions are answered in the affirmative, the prevention computing system 100 may conclude or presume that the disease is present, and therefore the expert rules engine 152 may focus on quantifying to what extent the disease has progressed, instead of asking questions to confirm its existence. The expert rules engine 152 can then try to determine how much of the disease is present, and the questioning may begin to follow a pattern to quantify the manifest effects. The system uses past answers to process the next questions, based on rules sets that are pre-established for the questions. Thus, the prevention system accumulates knowledge and domain expertise with the data provided from questioning. The system gathers data as it goes along to gain intelligence, which is derived from the information given to it, and then it utilizes this knowledge to develop and make recommendations, offer solutions based on the fact patterns given to it and render effective advice and opinions.

In some embodiments, the expert rules engine 152 of the prevention computing system 100 may be enhanced by a body of knowledge in the treatment of addiction disorders. This knowledge may be accessed, for example, from the prevention data source 156 or from other third-party data sources (e.g., data sources 166 described with reference to FIG. 7). Each addiction disorder presents unique and differing circumstances across many variables, yet in many ways the disease follows a pattern that can be mapped and quantified. While circumstances vary to a great degree, the disease itself can be broken down into progress segments and categorized based on type and the degrees of severity. The prevention computing system 100 and/or prevention data store 156 stores detailed experiential knowledge and treatment responses which the system accesses. As various details are provided through the input process, the expert rules engine 152 learns about the recipient and finds correlations with established standards of disease progression. The expert rules engine 152 can then create and recommend conclusions based on its knowledge and input received from, for example, the host and/or participants. As it receives input the prevention computing system 100 learns, and determines and/or generates the way to solve the problem. The expert rules engine 152 assess what missing information to request so that it can complete its intake process and then formulate a response that is appropriate and yet custom and specific to the person. The expert rules engine 152 utilizes if-then reasoning and logic to gather input and know which questions to ask and not to ask. Thus, the expert rules engine 152 can decipher important personal data and match it with corresponding action solutions.

The expert rules engine 152 may also be configured to implement fault detection techniques. For example, the expert rules engine 152 may evaluate answers and infer intent in order to determine if the answer likely to be authentic. If individual responses vary from expected behavior the expert rules engine 152 can ascertain that the response is not genuine or is a hoax. This is especially important in circumstances where third parties may be reporting about a person that appears to be at high risk. The expert rules engine 152 may also be able to measure the acuteness of certain responses to key questions, so that high-risk situations and other variations can be flagged for recommended action that is specific and appropriate to the circumstances.

Figure 2:
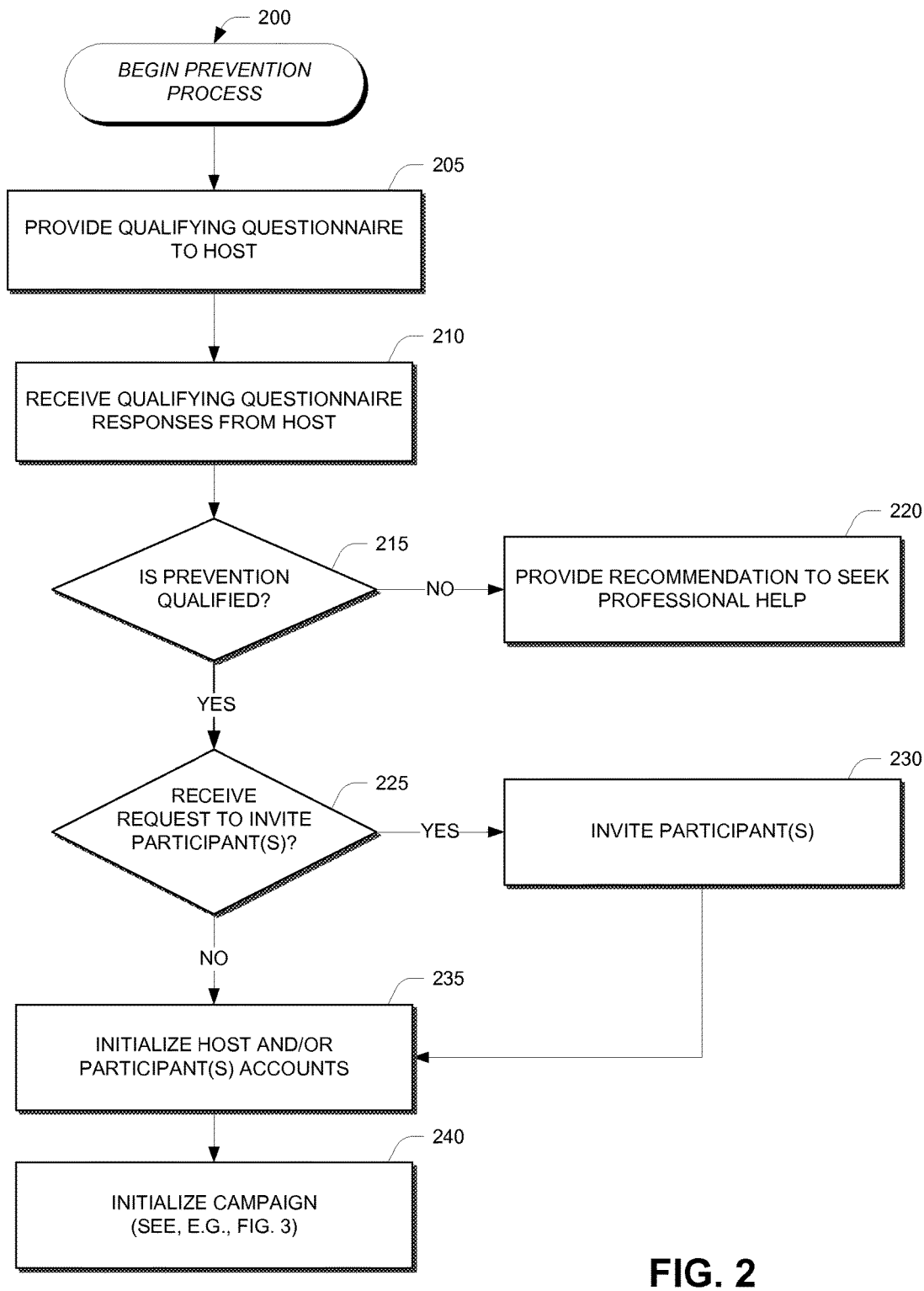
FIG. 2 schematically illustrates a logical flow diagram of a process for an individual, such as a host, to initiate a prevention campaign for a recipient, involving an embodiment of a prevention computing system, such as the prevention computing system of FIG. 1.

FIG. 2 is a logical flow diagram of a process 200 for an individual, such as a host, to initiate a prevention campaign for a recipient, involving an embodiment of a prevention computing system, such as the prevention computing system 100 of FIG. 1. The method of FIG. 2 will be described herein as being performed by the prevention computing system 100 and/or its components, but in other embodiments the method may be performed by one or more other computing systems, possibly in cooperation with the prevention computing system 100. In one embodiment, the process or routine can be dynamic, with some procedures omitted and others added.

Beginning at block 205, the prevention computing system 100 may provide a qualifying questionnaire to a host, for example via a web-based user interface as generated by user interface module 152, to acquire initial information about a recipient and the recipient's condition. At block 210, the prevention computing system 100 receives responses to the qualifying questionnaire from the host. At block 215, the prevention computing system 100 determines whether a prevention is qualified, based at least in part on the received responses to the qualifying questionnaire. For example, based on the responses, the prevention computing system 100 may determine that the recipient's condition is too serious for a prevention. Thus, at block 220, the prevention computing system 100 may, in response to a determination that the prevention is not qualified, provide a recommendation to the host to seek professional help. This in itself may be of significant value to the host, who might not otherwise suspect that the intended recipient's condition has progressed to the point at which professional help is the preferred or recommended solution.

If the prevention computing system 100 determines that the prevention is qualified, the process 200 may proceed to block 225 where the prevention computing system 100 determines whether it has received a request to invite participants to the prevention. For example, the host may provide the request to invite participants before, during, or at the conclusion of the qualifying questionnaire process. The request to invite participants may include the necessary contact information (e.g., name, email address, phone number, etc.) to enable the prevention computing system 100 to send invitations to the participants. If the prevention computing system 100 determines that a request to invite participants has been received, then at block 230 prevention computing system 100 may invite the participants, for example by sending an invitation email or similar communication to the participant(s) inviting them to join the prevention and create an account with the prevention computing system 100.

At block 235, the prevention computing system 100 initializes accounts for the host and/or any invited participants. Account information may be stored, for example, in the campaign and/or profile data store 158. At block 240, the prevention computing system 100 may initialize the campaign on behalf of the host and/or participants. The campaign process is illustrated and described in more detail with reference to FIG. 3 herein.

Figure 3:
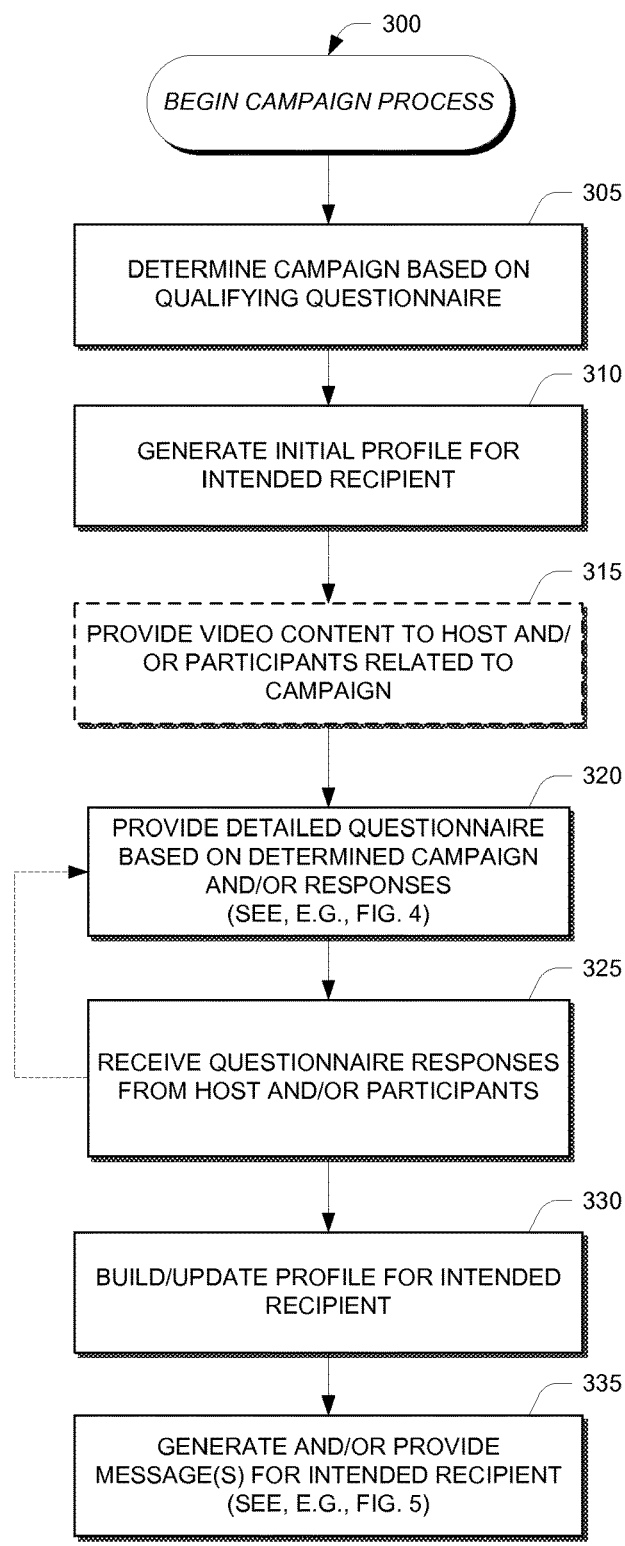
FIG. 3 is a logical flow diagram of a process 300 for beginning a campaign process on behalf of a host and/or participants, involving an embodiment of a prevention computing system, such as the prevention computing system of FIG. 1.

FIG. 3 is a logical flow diagram of a process 300 for beginning a campaign process on behalf of a host and/or participants, involving an embodiment of a prevention computing system, such as the prevention computing system 100 of FIG. 1. The method of FIG. 3 will be described herein as being performed by the prevention computing system 100 and/or its components, but in other embodiments the method may be performed by one or more other computing systems, possibly in cooperation with the prevention computing system 100. In one embodiment, the process or routine can be dynamic, with some procedures omitted and others added.

At block 305, the prevention computing system 100 determines a campaign (or type of campaign) based on a qualifying questionnaire (e.g., such as the qualifying questionnaire as described with reference to the process 200 in FIG. 2). This process involves, for example, determining which, if any, campaign definition is suitable for the host, and establishing any keyword filters to be applied to the detailed questionnaire and question sets in the campaign definition. Keyword filters in question sets may be used to tailor the detailed questionnaire to the specific conditions of the campaign. For example, if the qualifying questionnaire reveals that the recipient is not working, then questions asking about employment or co-workers may not be presented in subsequent detailed questionnaire and/or question sets.

At block 310, the prevention computing system 100 generates an initial profile for the intended recipient. The profile may be stored and accessed from, for example, the campaign and/or profile data store 158, and may be linked to the host and/or participant accounts and/or profiles.

At block 315, the prevention computing system 100 may optionally provide video content to the host and/or participants related to the campaign. For example, video content may be provided based on an initial assessment about the recipient's condition or problem, including education and background information about the condition or problem, possible treatments for the condition or problem, concerns and cautions to be aware of during a prevention and/or intervention process, and other related information. The video content may be stored and accessed from, for example, the prevention data source 156, or from another data source. In some embodiments the video content may be provided to the host and/or recipients at earlier stages of the prevention campaign, such as before, during, or after completion of the qualifying questionnaire, before the host and/or participants create accounts, or any other time before, during, or after the prevention campaign which may be appropriate.

At block 320, the prevention computing system 100 generates and provides a detailed questionnaire (e.g., questions and/or question sets) based on the determined campaign. For example, the questions presented in the detailed questionnaire may depend on factors that are determined during the qualifying questionnaire, including for example (1) the campaign type or type of problem/condition (e.g., alcohol abuse, drug abuse, etc.); (2) the relationship between the host and/or participants and the recipient (e.g., family member, friend, co-worker, etc.); and (3) character traits of the participant (e.g., serious, casual, religious, authoritative, etc.). Additional detail about the question generation process, as driven by, for example, the expert rules engine 150, is illustrated and described with reference to FIG. 4 herein.

Presentation of the questionnaire can vary depending on the implementation. For example, questions may be grouped together in a question set. A question set may include one or more questions that are related to a specific line of thought. Questions may also be further divided into page groups. A page group can be used to designate a series of questions that can be placed together on a single page (e.g., a web page displayed as part of a user interface for the questionnaire, generated for example by the user interface module 152). Data related to the questionnaires, questions, question sets, and/or page group may be stored and accessed, for example, in the prevention data source 156.

At block 325, the prevention computing system 100 receives responses to the questionnaire from the host and/or participants. In one embodiment, the questionnaire does not need to be completed in one sitting. The host/participant may leave and return at any time during the questionnaire and resume where he/she left off. In some embodiments, the user may go back to a previously asked question and change an answer if needed at any time during the questionnaire. In some embodiments, the host and participant may communicate with each other via a messaging and chat system on the site. In one embodiment, participants may only communicate with the host, but not with each other.

As the responses are received, the prevention computing system 100 may process and use the responses to generate subsequent questions in the questionnaire. Thus, for example, the process 300 may return to block 320 and repeat blocks 320 and 325 an indeterminate number of times to determine and provide subsequent questions in the questionnaire which are appropriate based on prior received responses. Additional detail about how the responses may be used to inform the question generation process, as driven by, for example, the expert rules engine 150, is illustrated and described with reference to FIG. 4 herein.

At block 330, the prevention computing system 100 builds or updates a profile for the intended recipient based, for example, on the received responses. For example, the responses received by the prevention computing system 100 may be stored in the campaign and/or profile data source 158, for example, as part of the prevention campaign associated with the host or recipient. The responses may then be accessed for use in either the questionnaire process and/or the message generation process.

At block 335, the prevention computing system 100 can generate one or more messages for the intended recipient. The messages may be generated, for example, once the host and/or participants have completed the questionnaire process and the prevention computing system 100 has received the responses. Additional detail about the message generation process, as driven by, for example, the expert rules engine 150 and/or messaging module 154, is illustrated and described with reference to FIG. 5 herein. Once the messages have been generated, the host may select one or more messages (see, e.g., FIG. 5 herein) for the prevention computing system 100 to provide or send to the recipient (see, e.g., FIG. 6 herein).

Figure 4:
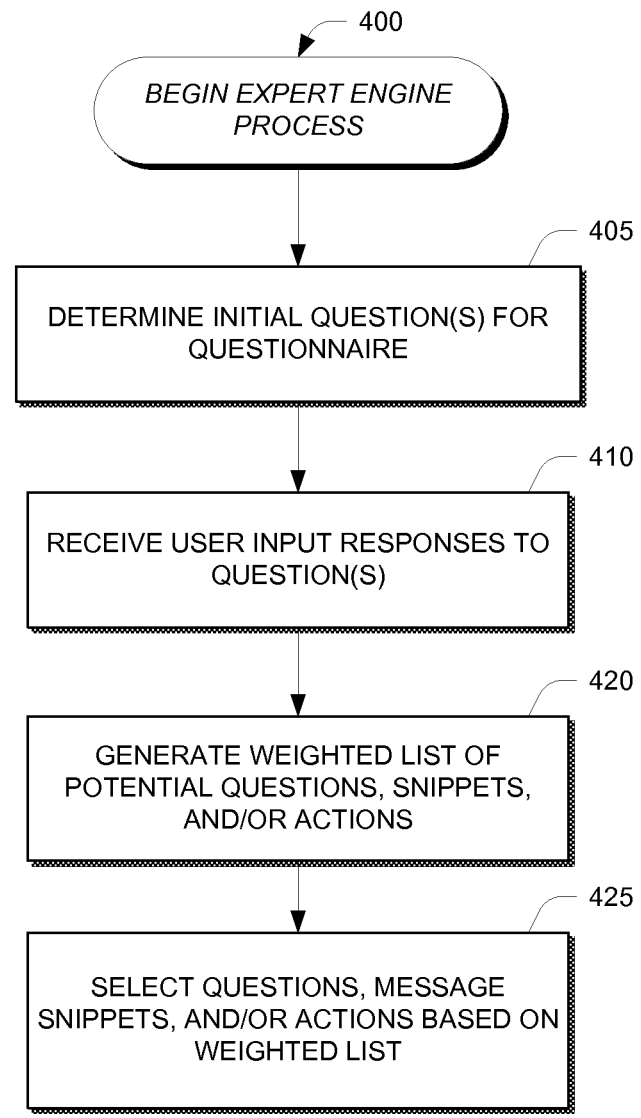
FIG. 4 is a logical flow diagram of a process 400 involving an expert engine to generate questions and/or actions for a prevention campaign, involving an embodiment of a prevention computing system, such as the prevention computing system of FIG. 1.

FIG. 4 is a logical flow diagram of a process 400 involving an expert engine to generate questions and/or actions for a prevention campaign, involving an embodiment of a prevention computing system, such as the prevention computing system 100 of FIG. 1. The method of FIG. 4 will be described herein as being performed by the prevention computing system 100 and/or its components, but in other embodiments the method may be performed by one or more other computing systems, possibly in cooperation with the prevention computing system 100. In one embodiment, the process or routine can be dynamic, with some procedures omitted and others added.

With reference to the process 400 described below, the following listing provides one example implementation of the structure of a question which may be used to facilitate the dynamic generation of questions and/or actions for a detailed questionnaire according to one embodiment:

ID: a unique identifier for the question

Order: a numeric value which determines the order in which the question is presented during the questionnaire. Questions with lower order numbers are presented before questions with higher order numbers. It is possible for questions to have equal order numbers in which case the order is not defined.

Question Tag-Weights: The tag-weight is a keyword and weight value pair that is assigned to the question. In this case, the weight acts as a threshold value. The question is activated if the campaign tag table contains the tag weighted at or higher than this threshold. If the campaign tag table does not contain the tag, or is weighted lower than the threshold, then the question is not activated for the campaign.

Type: A question type may be one of, for example, TEXT, TEXTBOX, RADIO, CHECKBOX, SELECTION.

Question: Contains the question text presented to the user.

Options: For question types that require options (e.g., RADIO, CHECKBOX, SELECT, etc.), these are the list of options. Each option contains a text and key parameter. For TEXT and TEXTBOX question types, the options contain a list of keywords. If a keyword matches any of the input text, the option is considered selected. In this case, multiple option selections are possible.

Option Tag-Weights: The option tag-weight is a keyword and weight value pair that is assigned to an option value. Options can have more than one tag-weight pair. If the option is selected, the tag is added to the campaign tag table. If the tag already exists in the campaign tag table, then the weight is added to the previous weight. Weights can be positive or negative.

Rule Condition: One of IS, ISNOT, CONTAINS, DOESNOTCONTAIN, LESSTHAN, LESSTHANEQUAL, MORETHAN, MORETHANEQUAL. Each question may have zero or more rules (condition/action pairs). Each rule condition is tested by comparing the rule parameter with the selected option or matching keyword. If the test succeeds, then the rule action is applied Rule Parameter: This text/numeric value is used to match the rule condition with the selected answer.

Rule Action: If the tested rule condition is successful, this action is applied. Actions are defined as needed and may be as simple "skip to question id#", or trigger a response event. Use cases for this would be to skip questions that don't apply to the current situation, or trigger events to activate programmed responses.

With reference now to FIG. 4, beginning at block 405, the prevention computing system 100 determines one or more initial questions for the detailed questionnaire to be provided to a host and/or participants. For example, the initial questions may be determined based on a campaign definition associated with the prevention campaign. For example, in one embodiment, the expert rules engine 152 may implement a tag table technique to generate filtered questions, messages, and actions. Each campaign may include a tag table per host and/or participant. The campaign tag table includes a list of tag or key words which may be used during the campaign. Each tag word contains a weight value that accumulates during the campaign. The tag table may be used to help determine or select which questions are included during the questionnaire, and also to help select message snippets to be included in the final message. The prevention computing system 100 may use the responses from qualifying questionnaire is to build the initial tag table. The tag table may then be used to select the campaign type and question sets for further questioning.

At block 410, the prevention computing system 100 receives user input responses to the questions presented via the questionnaire (e.g., as provided as part of the process 300 at block 325). Continuing the tag table example, each question response adds to the campaign tag table, such that over time the weight value accumulates.

At block 415, the prevention computing system 100 generates a weighted list of potential questions, message snippets, and/or actions, for example based on the received user input responses. Continuing the tag table example, the tag table may be used to filter questions in subsequent question sets based on tag weights associated with certain questions At block 420, the prevention computing system 100 selects questions, message snippets, and/or actions based on the weighted list. Continuing the tag table example, one or more messages can be generated by accessing message snippets from a database (e.g., the prevention data store 156) based on the highest thresholds for matching tags in the campaign tag table.

As one example of how the tag table may be implemented to inform the expert rule engine 152, during a questionnaire, a question may be asked regarding smoking (or, e.g., any other addiction-related illness or disorder, such as alcoholism, gambling, compulsive behavior, etc.). The affirmative option for the question may define a tag-weight for the tag "smoking" with a weight of "5." If answered in the affirmative, the "smoking" tag with weight "5" is added to the campaign tag table. A follow-up question may ask about the frequency of smoking. This question may include multiple select options with varying weights for the "smoking" tag. If the respondent selects "Two packs a day" this may add a weight of "50" to the "smoking" tag in the campaign tag table, so the "smoking" tag is now weighted at "55." For subsequent question sets, questions that contain a question tag-weight tag for "smoking" are only activated if the tag-weight threshold is below "55." These question sets may add additional tags to the campaign tag table such as "hospitalization", "cancer risk," or "overdosed" each with an accumulated weight. When the message is generated, snippets are queried (e.g., from the prevention data source 156) for matching tags from the campaign tag table and selected by their highest threshold value that is not higher than the tag weight.

Examples of Message Generation, Delivery, and Follow-Up Methods Performed by a Prevention Computing System One benefit of the prevention computing system 100 is that it can produce a set of well written messages that appear to have been written by the host and/or participants and express the host and/or participants' wishes. The messages may be professionally designed to encourage the recipient to seek help. Message variety may be obtained by drawing from a pool of message snippets to formulate the message. Message snippets may be stored in a database (e.g., the prevention data source 156) and may include attributes that categorize the snippet by campaign type, relationship of participant to recipient, character of participant, and component of the message which determines the order the snippet is placed in the message. A message may include several components, including for example a salutation, an introduction, a position, evidence, counter arguments, a call to action, and a signature. Each snippet may have multiple versions, each version using different words to say the same thing. The prevention computing system 100 and messaging module 154 may be configured to ensure that any snippet is used only once in a campaign, such that every message in the campaign is unique.

The prevention computing system 100 offers myriad choices of output messages based on the many input criteria provided during the input questioning process described above. The host may also able to customize the messages with style choices and confirm fact patterns that have been established by the previously provided data during the questionnaire process. Details about the relationships from the host and each of the participants enable the system to tailor the messages to the recipient with the appropriate vernacular that would be customary to that relationship. For example the prevention computing system 100 can differentiate, and generate different messages from, a child to a recipient that has a distant relationship with the child (e.g., because of a divorce and subsequent separation from the child) versus a child that has had a close relationship with a fully engaged parent. The prevention computing system 100 can differentiate recommendations based on relationship, gender characteristics, age, marital status, relationship history, experiential facts, as well as circumstantial and social dynamics. The prevention computing system 100 further differentiates such details as the history of the destructive activity, the family history with the disease, the current living dynamics and relationship dynamics, addiction history, treatment history, severity assessment, financial evaluations, etc. The prevention computing system 100 can detect personal fact patterns about the recipient's circumstances and risk features, and then identify correlating content in its messaging data store (e.g., as stored in prevention data source 156) as well as its video testimonial content library (e.g., as stored in prevention data source 156) to match the recipient's circumstances with an appropriate message or video to achieve the optimum impact.

In some embodiments, the prevention computing system 100 follows a message output pattern that mirrors effective methods and processes in addiction treatment. For example, the process establishes the place of love and care that the host and participants are coming from, offers a sympathetic connection to establish trust and to disarm the recipient, clarifies the problems that the disease is causing, in certain instances recalls better times to establish a key reference point for the recipient, addresses how the disease has taken a hold of the person, provides examples of how this has happened, and genuinely asks the person to accept the gift of help.

In some embodiments, the prevention computing system 100 enables the host to create an action plan that recommends to the recipient the next step to take if they agree to get help. The messaging module 154 may combine the extensive information gathered about the recipient from the questioning, and then gives the senders a series of choices from drop down menu options based on the input provided and knowledge the system has gained to enable them to create a truly customized and personal message that is impactful.

Figure 5:
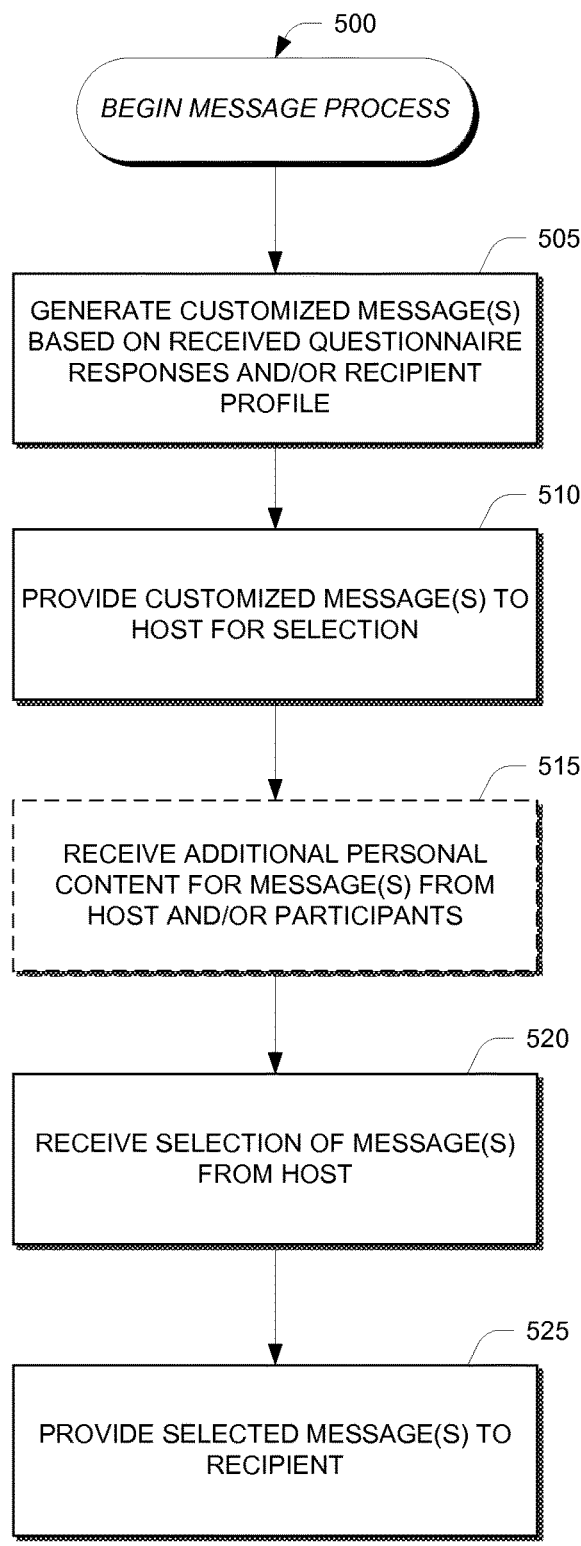
FIG. 5 is a logical flow diagram of a process 500 for generating one or more messages for a recipient as part of a prevention campaign, involving an embodiment of a prevention computing system, such as the prevention computing system of FIG. 1.

FIG. 5 is a logical flow diagram of a process 500 for generating one or more messages for a recipient as part of a prevention campaign, involving an embodiment of a prevention computing system, such as the prevention computing system 100 of FIG. 1. The method of FIG. 5 will be described herein as being performed by the prevention computing system 100 and/or its components, but in other embodiments the method may be performed by one or more other computing systems, possibly in cooperation with the prevention computing system 100. In one embodiment, the process or routine can be dynamic, with some procedures omitted and others added.

At block 505, the prevention computing system 100 generates one or more customized messages based on the received questionnaire responses and/or a recipient profile. The messages may be generated dynamically, for example by the expert rules engine 150, using similar techniques or algorithms as described with reference to FIG. 4. For example, the tag-weighting approach described above may be used to retrieve message snippets (e.g., from the prevention data source 156) for matching tags from a tag table for the campaign and selected by their highest threshold value that is not higher than the tag weight.

At block 510, the prevention computing system 100 provides the customized messages to the host for selection. The host may also be prompted to provide an indication of the order and/or frequency of which the customized messages are to be delivered to the recipient. The order and/or frequency may also be determined based on a service level for which the host is subscribed. For example, a basic subscription level may allow the host to select up to three messages (or any other number) to be delivered once per week (or any other periodic basis), while an advanced subscription level may allow the host to select all customized messages with a preferred order and delivery schedule. Any variation on the subscription level may be possible. In some embodiments the order and frequency may be determined as part of the campaign definition or as determined by a preventionist involved in the prevention campaign.

In some embodiments, the host may be subscribed to or otherwise have access to a preventionist as part of the prevention campaign. At block 515, as part of such a service, the host and/or participants may be provided the option to provide additional personal content to be included in the customized message(s) to the recipient. For example, audio and/or video recordings, personal notes, and the like may be received by the prevention computing system 100 to be included with the customized messages. In some embodiments, the preventionist involved in the prevention campaign may then assist the host in determining whether any such personal content should be included with the messages.

At block 520, the prevention computing system 100 receives the selection of message(s) from the host. The prevention computing system 100 may also receive with the selection delivery preferences (e.g., order, frequency) as described above. At block 525, the prevention computing system 100 provides the selected message(s) to the recipient. Additional detail about how the messages may be provided to the recipient, as driven by, for example, the messaging module 154, is illustrated and described with reference to FIG. 6 herein.

Figure 6:
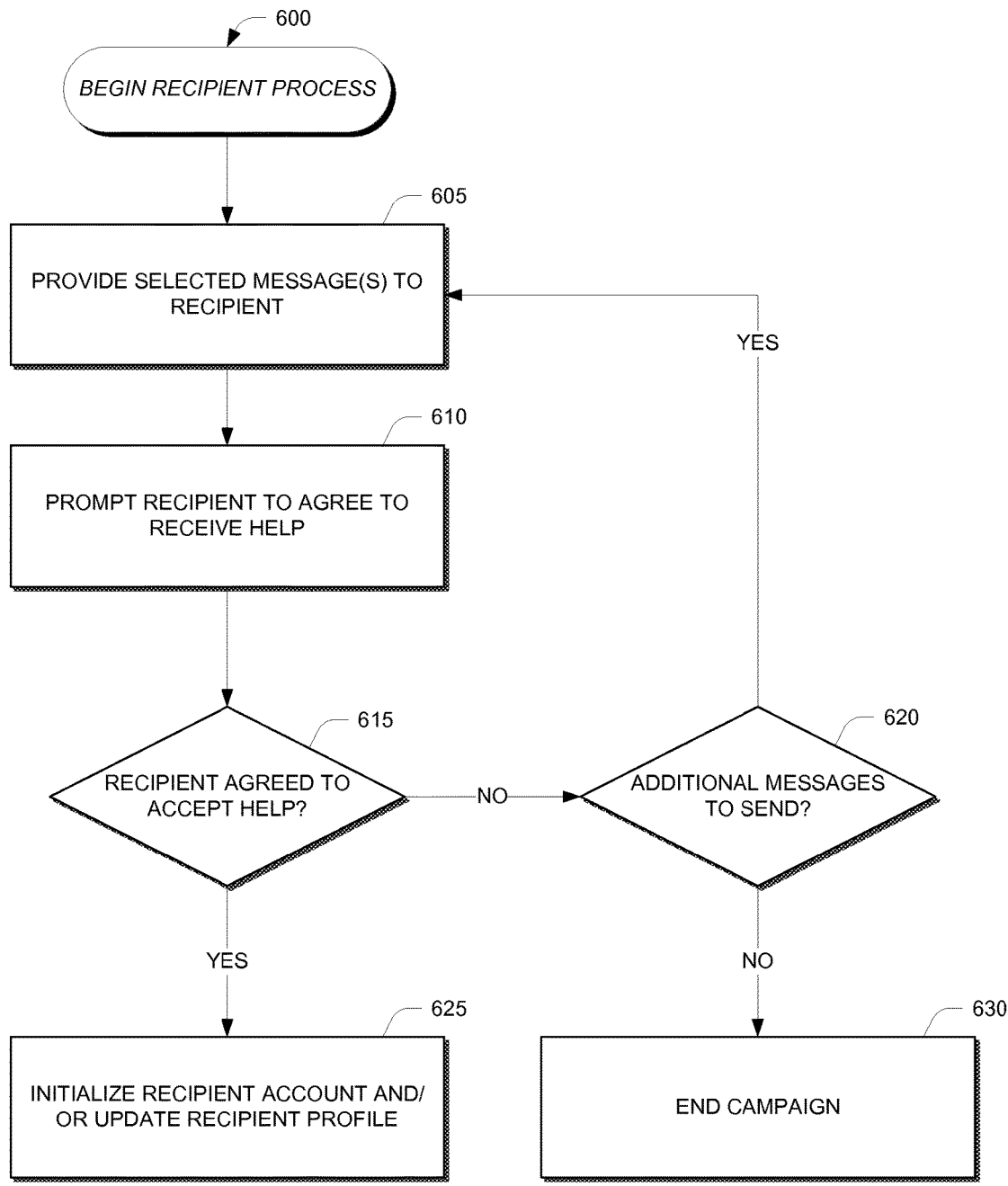
FIG. 6 is a logical flow diagram of a process 600 for providing one or more messages for a recipient as part of a prevention campaign, involving an embodiment of a prevention computing system, such as the prevention computing system of FIG. 1.

FIG. 6 is a logical flow diagram of a process 500 for providing one or more messages for a recipient as part of a prevention campaign, involving an embodiment of a prevention computing system, such as the prevention computing system 100 of FIG. 1. The method of FIG. 6 will be described herein as being performed by the prevention computing system 100 and/or its components, but in other embodiments the method may be performed by one or more other computing systems, possibly in cooperation with the prevention computing system 100. In one embodiment, the process or routine can be dynamic, with some procedures omitted and others added.

At block 605, the prevention computing system 100 provides the selected message(s) to the intended recipient of a prevention campaign. The message(s) may be provided for example, by an email or text message sent to the recipient. In some embodiments, the email or text message may direct the recipient to a web site and not include any personal information in the message itself. Once the recipient accesses the web site, he/she may be prompted to verify their identity by answering a personal question arranged by the host. If the identity is verified, the prepared message may be viewed by the recipient. The message(s) may include, for example, customized messages generated as part of the process 500 described with reference to FIG. 5 herein. The prevention computing system 100 may also provide a notification to the host, participant, and/or preventionist that the message has been provided or delivered to the recipient. In some embodiments, prevention computing system 100 may detect whether the recipient has read the message and provide such indication to the host, participant, and/or preventionist as well.

At block 610, the prevention computing system 100 may prompt the recipient to agree to receive help. In some embodiments, the prompt to agree to receive help may be provided as part of the message content itself. For example, the message may include an actionable option or link to agree to receive help, which may direct the recipient viewing the message to a prevention website, for example as provided by the prevention computing system 100. In other embodiments, the message may direct the recipient to a web site to view more information and/or additional messages, at which time the prompt to agree to receive help may be provided as part of a web page presented to the recipient. In some embodiments, the message(s) provided to recipient may also include an action plan (or a first step of an action plan) that recommends to the recipient the next step to take if they agree to get help. In other instances, the action plan may not be provided to the recipient until after they agree to get help.

At block 615, the prevention computing system 100 determines whether the recipient has agreed to accept help. The determination might be made after the recipient expressly agrees or refuses to accept help (e.g., by some action, such as clicking on a link or option presented as described at block 610), or after a specified period of time has elapsed without receiving any kind of response or indication from the recipient to agree to accept help.

If the prevention computing system 100 determines that the recipient has agreed to accept help, then at block 625 the prevention computing system 100 may initialize an account for the recipient and/or update the recipient profile associated with the prevention campaign and/or host or participant profiles. Once the recipient creates an account he/she may join the campaign to follow-up and report progress. In one embodiment, the prevention computing system 100 may then provide or display an action plan (or a first step of an action plan) that recommends to the recipient the next step to take. For example, information may be provided to help the recipient find the necessary resources in his/her local area, or the recipient may be connected with a counselor to receive help. In some embodiments, the prevention computing system 100 may trigger a confidential message to the host, participant, and/or preventionist indicating that the recipient has agreed to get help.

If the prevention computing system 100 determines that the recipient has not agreed to accept help, then at block 620 the prevention computing system 100 may determine whether there are additional messages to send to the recipient. The prevention computing system 100 may also provide a notification to the host, participant, and/or preventionist that the recipient has read the message but has not agreed to accept help. If there are additional messages to send to the recipient, the process 600 may return to block 605 and continue making attempts to reach the recipient by sending additional message(s), repeating blocks 605, 610, 615, and 620 an indefinite number of times until there are no more messages to provide to the recipient. For example, the prevention computing system 100 may first send a message from the host, followed by one or more messages from the participants and/or preventionist, or followed by additional messages from the host, in any order and/or frequency as determined by the host and/or preventionist during the message selection process (see, e.g., FIG. 5) or as determined by the host's subscription level. In some embodiments the initial message that is delivered may be sent again with formatting adjustments to accommodate for the appearance of uniqueness. The frequency of delivery may be established based on the parameters identified in the input criteria (e.g., as part of the questionnaire process) and the recipient's circumstances, with the goal of an increased success rate from the call to action.

Once the prevention computing system 100 determines that there are no additional messages to send to the recipient, the process 600 may proceed to block 630, where the prevention computing system 100 may end the campaign. Ending the campaign may trigger the prevention computing system 100 to provide a notification to the host, participants, and/or preventionist that the recipient has not agreed to receive help (e.g., either by ignoring all messages sent or by actively refusing to receive help).

Example System Implementation and Architecture

Figure 7:
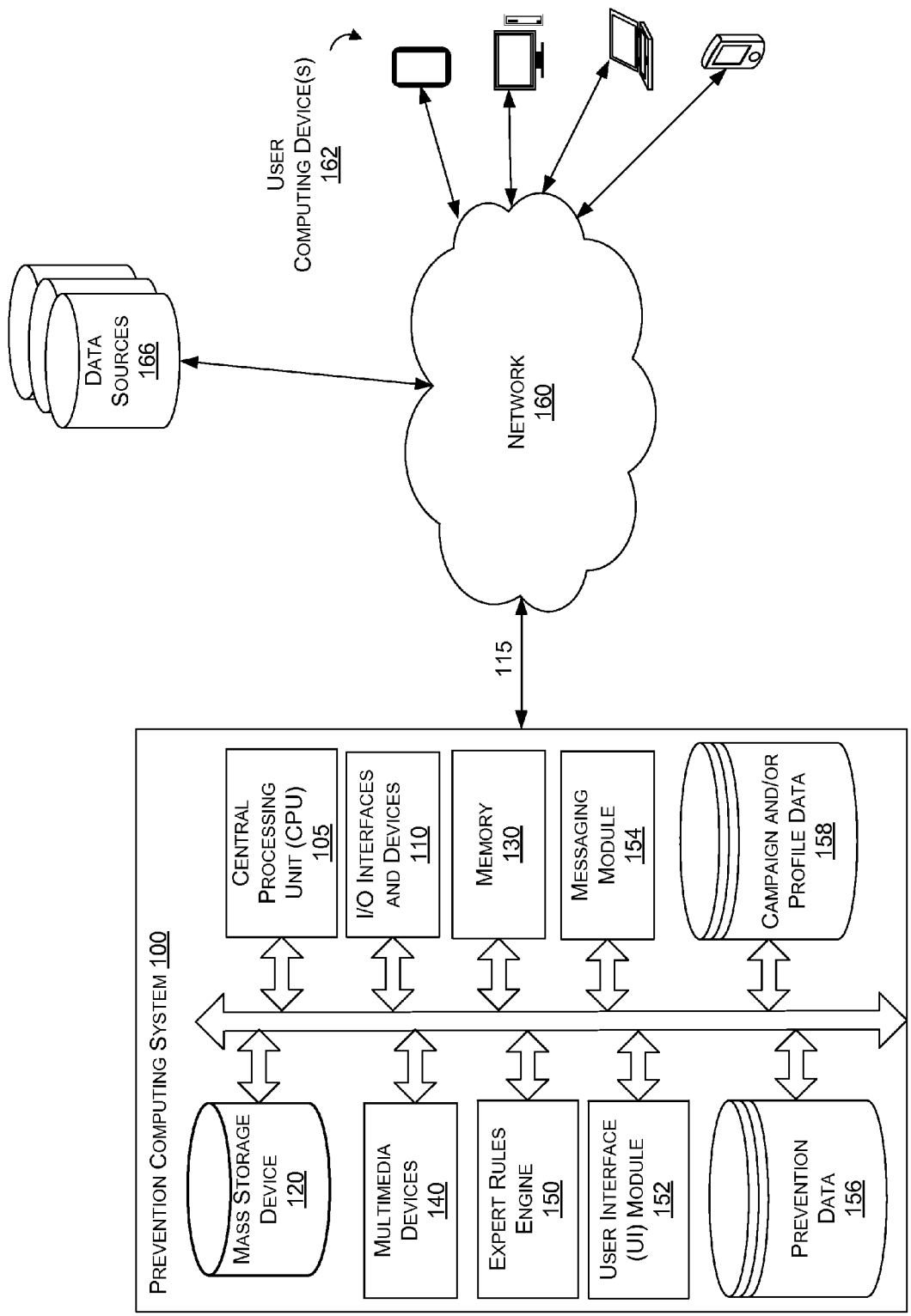
FIG. 7 is a block diagram showing an embodiment in which a prevention computing system is in communication with a network, and various systems, such as user computing devices, are also in communication with the network.

FIG. 7 is a block diagram showing an embodiment in which a prevention computing system 100 is in communication with a network 160, and various systems, such as user computing device(s) 162 are also in communication with the network 160. The prevention computing system 100 may be used to implement systems and methods described herein.

In the embodiment of FIG. 7, the prevention computing system 100 includes an expert rules engine 150, a user interface module 152, and a messaging module 154, a prevention data source 156, and/or a campaign and/or profile data source 158. The expert rules engine 150 may be configured to implement the processes for dynamic questionnaire and message generation as described herein, for example with reference to FIGS. 2-4. The messaging module 154 may be configured to implement the processes for message generation and delivery to recipients as described herein, for example with reference to FIGS. 4-6. The prevention data source 156 may store, for example, subject matter data for a variety of disorders, expert or knowledge-based rules related to the subject matter data, and/or predefined questions. The campaign and/or profile data source 158 may store, for example, data related to campaigns, hosts, participants, recipients, including questions and answers/responses to questionnaire and related data. In some embodiments, such as the embodiment of the prevention computing system 100 shown in FIG. 1, the prevention data source 156 and campaign and/or profile data source 158 may be a stand-alone data stores.

In the particular embodiment of FIG. 7, the prevention computing system 100 includes a user interface module 152 configured to generate and provide user interfaces described herein for an individual (e.g., a host, a participant, a prevention specialist, and/or a recipient) accessing a prevention computing system, such as via a web browser or standalone application. In some embodiments the dashboard/user interface module 152 may also be configured to generate user interfaces for alerts and/or mobile user interfaces provided to the user such as a host, participant, and/or recipient in communication with the prevention computing system 100.

The computing system 100 includes, for example, a personal computer that is IBM, Macintosh, or Linux/Unix compatible or a server or workstation. In one embodiment, the prevention computing system 100 comprises a server, a laptop computer, a smart phone, a personal digital assistant, a kiosk, or an media player, for example. In one embodiment, the exemplary computing system 100 includes one or more central processing unit ("CPU") 105, which may each include a conventional or proprietary microprocessor. The prevention computing system 100 further includes one or more memory 130, such as random access memory ("RAM") for temporary storage of information, one or more read only memory ("ROM") for permanent storage of information, and one or more mass storage device 120, such as a hard drive, diskette, solid state drive, or optical media storage device. Typically, the modules of the prevention computing system 100 are connected to the computer using a standard based bus system. In different embodiments, the standard based bus system could be implemented in Peripheral Component Interconnect ("PCI"), Microchannel, Small Computer System Interface ("SCSI"), Industrial Standard Architecture ("ISA") and Extended ISA ("EISA") architectures, for example. In addition, the functionality provided for in the components and modules of computing system 100 may be combined into fewer components and modules or further separated into additional components and modules.

The prevention computing system 100 is generally controlled and coordinated by operating system software, such as Windows XP, Windows Vista, Windows 7, Windows 8, Windows Server, Unix, Linux, SunOS, Solaris, iOS, Blackberry OS, or other compatible operating systems. In Macintosh systems, the operating system may be any available operating system, such as MAC OS X. In other embodiments, the prevention computing system 100 may be controlled by a proprietary operating system. Conventional operating systems control and schedule computer processes for execution, perform memory management, provide file system, networking, I/O services, and provide a user interface, such as a graphical user interface ("GUI"), among other things.

The exemplary computing system 100 may include one or more commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, a display device provides for the presentation of GUIs, application software data, and multimedia presentations, for example. The prevention computing system 100 may also include one or more multimedia devices 140, such as speakers, video cards, graphics accelerators, and microphones, for example.

In the embodiment of FIG. 7, the I/O devices and interfaces 110 provide a communication interface to various external devices. In the embodiment of FIG. 7, the prevention computing system 100 is electronically coupled to the network 160, which comprises one or more of a LAN, WAN, and/or the Internet, for example, via a wired, wireless, or combination of wired and wireless, communication link 115. The network 160 communicates with various computing devices and/or other electronic devices via wired or wireless communication links.

According to FIG. 7, in some embodiments, information may be provided to and/or accessed by the prevention computing system 100 over the network 160 from one or more data sources 166 (add to FIG. 7?). The data sources 166 may include one or more internal and/or external data sources. The data sources 166 may include internal and external data sources which store, for example, health and/or medical subject matter data (e.g., addiction/disorder/disease data), addiction and/or other intervention data, and the like. In some embodiments, one or more of the databases or data sources 156, 158, and/or 166, may be implemented using a relational database, such as Sybase, Oracle, CodeBase and Microsoft® SQL Server as well as other types of databases such as, for example, a flat file database, an entity-relationship database, and object-oriented database, and/or a record-based database.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the prevention computing system 100, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Other

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y and Z," unless specifically stated otherwise, is to be understood with the context as used in general to convey that an item, term, etc. may be either X, Y or Z, or a combination thereof. Thus, such conjunctive language is not generally intended to imply that certain embodiments require at least one of X, at least one of Y and at least one of Z to each be present.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by the prevention computing system 100 and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. An automated addiction recovery assistance system designed to assist individuals suffering from addictions to begin a recovery process, the system comprising:
   one or more hardware processors in communication with a memory storing executable instructions, wherein the one or more hardware processors are configured to execute the executable instructions that cause the one or more hardware processors to:
      determine an addiction profile for a recipient individual, the addiction profile determined by comparison with addiction profiles of a plurality of individuals accessed from an addiction profile database, wherein the addiction profile comprises data for a possible addiction disorder from which the recipient individual may suffer and a plurality of participant individuals associated with the recipient individual; and
      for each of the plurality of participant individuals:
         retrieve, from the addiction profile, a keyword tag-weight table mapping an at least one keyword associated with the possible addiction disorder to a keyword weight indicative of a relative strength of association with the possible addiction disorder to the recipient individual;
         access, from addiction disorder database stored in the memory, a plurality of potential message portions based on the recipient individual's addiction profile;
         compare the keyword weight to each of a respective plurality of tag-weights associated with the respective plurality of potential message portions;
         select a message portion from the plurality of potential message portions based on the comparison;
         customize the selected message portion based on a relationship type between the respective participant individual and the recipient individual; and
         generate a message from the respective participant individual to the recipient individual, wherein the message includes at least the customized selected message portion.

2. The system of claim 1, wherein the customization further comprises determining a type of addiction from which the recipient individual may be suffering, or a type of character associated with the respective participant individual and customizing the selected message portion based on the determination of the type of addition or the type of character.

3. The system of claim 2, wherein the customization comprises generating a vernacular that is particular based on whether the relationship between the respective participant individual and the recipient individual is one of parent-child, husband-wife, friend, co-worker, boss, sibling, relative, religious affiliate, student-teacher, or other addiction sufferer.

4. The system method of claim 2, wherein the customization comprises generating a vernacular that is particular based on whether the relationship between the respective participant individual and the recipient individual is characterized by a relative age difference, a family relationship, a prior history of joint addiction or abuse, a prior history of treatment, a common genetic trait, a common marital status, or other degree of closeness factor.

5. The system of claim 1, wherein the executable instructions when executed by the one or more hardware processors further cause the one or more hardware processors to:
   provide, to a host individual, each message from the respective participant individuals to the recipient individual;
   receive, from the host individual, a selection of at least one of the messages from the respective participant individuals for delivery to the recipient individual; and provide, to the recipient individual, the at least one selected message.

\* \* \* \* \*